(12) United States Patent
Hohl et al.

(10) Patent No.: US 12,702,377 B2
(45) Date of Patent: Aug. 11, 2026

(54) COMPUTED TOMOGRAPHY SYSTEM WITH IMPROVED DATA TRANSMISSION

(71) Applicant: Siemens Healthineers AG, Forchheim (DE)

(72) Inventors: Christoph Hohl, Hahnbach (DE); Peter Michael Dueppenbecker, Herzogenaurach (DE); Markus Biele, Hetzles (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 108 days.

(21) Appl. No.: 18/889,519

(22) Filed: Sep. 19, 2024

(65) Prior Publication Data

US 2025/0099065 A1 Mar. 27, 2025

(30) Foreign Application Priority Data

Sep. 22, 2023 (EP) .................................... 23199109

(51) Int. Cl.
*A61B 6/00* (2024.01)

(52) U.S. Cl.
CPC .................................... *A61B 6/563* (2013.01)

(58) Field of Classification Search
CPC ...................................................... A61B 6/563
See application file for complete search history.

(56) References Cited

U.S. PATENT DOCUMENTS 5,148,448 A 9/1992 Karam et al.
7,599,467 B2 * 10/2009 Popescu .................. A61B 6/56 378/4
7,755,055 B2 * 7/2010 Schilling .................. A61B 6/56 250/370.09
7,899,149 B2 * 3/2011 Krumme ................. H04L 25/08 378/4
12,113,722 B2 * 10/2024 Urban ..................... H04L 67/12
12,502,155 B2 * 12/2025 Bergner ................. A61B 6/032

FOREIGN PATENT DOCUMENTS

EP 2932901 A1 10/2015

* cited by examiner

*Primary Examiner* — David J Makiya
(74) *Attorney, Agent, or Firm* — Harness, Dickey & Pierce, P.L.C.

(57) ABSTRACT

According to one or more example embodiments, a computed tomography system includes a first part; a second part, wherein the first part is rotatable relative to the second part around an axis of rotation; a plurality of first modems on the first part which are connected in a data-technical manner to first coupling elements on the first part; and a plurality of second modems on the second part which are connected in a data-technical manner to second coupling elements on the second part.

16 Claims, 6 Drawing Sheets

FIG 7
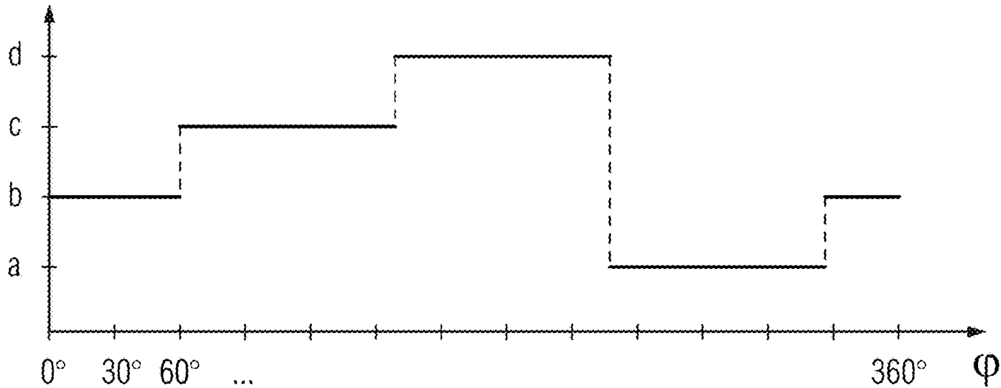
FIG 8
11
DS1
DS2
19
19
cos(CS)
sin(CS)
20
SS
12
FIG 9
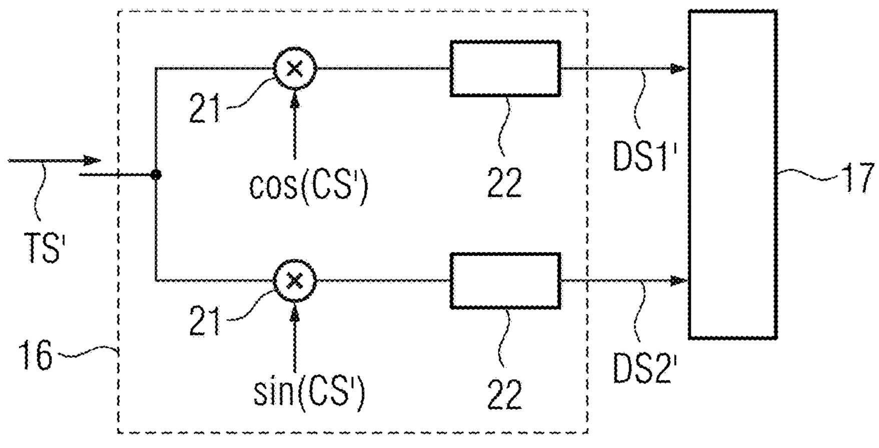

COMPUTED TOMOGRAPHY SYSTEM WITH IMPROVED DATA TRANSMISSION

CROSS-REFERENCE TO RELATED APPLICATION(S)

The present application claims priority under 35 U.S.C. § 119 to European Patent Application No. 23199109.2, filed Sep. 22, 2023, the entire contents of which are incorporated herein by reference.

Related Art

Computed tomography systems are generally known.

In a computed tomography system, an X-ray source and an X-ray detector are arranged on the gantry (rotating part), the X-ray source emitting X-rays and the X-ray detector capturing the emitted X-rays during the rotation of the gantry. Based on the images of an object of investigation (usually a person, in particular a patient) captured in this way, a three-dimensional image of the object of investigation is reconstructed.

The applicant points out that regardless of the grammatical gender of a particular personal term (such as here, for example, the term "patient"), persons with male, female and other gender identities are always included.

The three-dimensional image is reconstructed via an evaluation facility which is arranged outside the gantry, for example even outside the examination room, in which the computed tomography system is arranged. The image data captured via the X-ray detector must be transmitted to the evaluation facility during the rotation of the gantry. As a rule, this takes place via a transmission channel through which the digital data from a data source (for example, a pre-evaluation facility which slightly processes the captured data of the X-ray detector) is supplied to a modem which modulates the digital data onto a carrier signal. The modulated carrier signal is supplied to another modem via a transmission channel. The other modem is arranged on the base body (fixed part). It demodulates the modulated carrier signal and feeds the received signal determined in this way to a data sink. The data source and the associated modem are in this case arranged on the gantry, the other modem and the data sink on the fixed base body. The transmission channel thus forms the bridge between the gantry and the fixed base body.

With the constant development of computed tomography systems, the volume of data to be transmitted from the data source to the data sink continues to increase. Conventional types of data transmission are increasingly reaching their limits. Attempts are therefore being made to increase the data rate at which the data is transmitted.

SUMMARY

One or more example embodiments creates possibilities via which the data rate during data transmission between the gantry and the fixed base body can be increased for a given bandwidth of a transmission channel.

BRIEF DESCRIPTION OF THE DRAWINGS

Properties, features and advantages of one or more example embodiments will become clearer and more comprehensible in connection with the following description of the exemplary embodiments, which will be explained in more detail in connection with the drawings. Here, in a diagrammatic view, FIG. 7 shows an angle diagram according to one or more example embodiments, FIG. 8 shows a data source and a first modem according to one or more example embodiments, FIG. 9 shows a second modem and a data sink according to one or more example embodiments.

DETAILED DESCRIPTION

Figure 1:
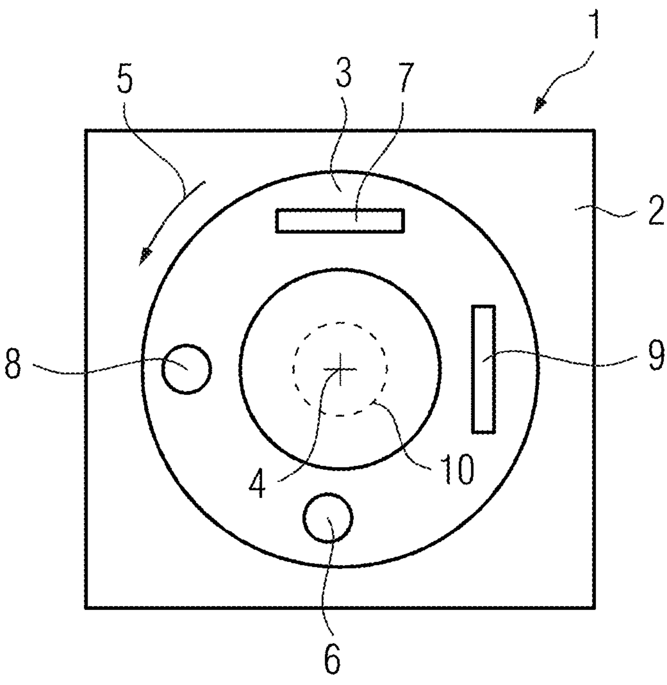
FIG. 1 shows a computed tomography system according to one or more example embodiments.

One or more example embodiments is based on an operating method for a computed tomography system,

- first data being transmitted via a plurality of first coupling elements arranged on the first part and a plurality of second coupling elements arranged on the second part during a rotation of a first part of the computed tomography system relative to a second part of the computed tomography system around an axis of rotation between a plurality of first modems arranged on the first part and a plurality of second modems arranged on the second part,
- the first coupling elements extending over a respective first angular range when viewed in the circumferential direction around the axis of rotation,
- the first angular ranges, viewed from the first coupling element to the first coupling element, being disjoint in relation to one another and, viewed over the entirety of the first coupling elements, forming a full circle around the axis of rotation,
- the second coupling elements extending over a respective second angular range as viewed around the axis of rotation,
- the second angular ranges, as viewed around the axis of rotation, being disjoint in relation to one another and spaced apart from one another, in particular evenly distributed around the axis of rotation,
- so that the second coupling elements each couple with the first coupling element in whose first angular range the second angular range of the respective second coupling element is currently located.

One or more example embodiments is furthermore based on a computed tomography system,

- the computed tomography system comprising a first and a second part, the first part being rotatable relative to the second part around an axis of rotation, a plurality of first modems being arranged on the first part, which are connected in a data-technical manner to first coupling elements arranged on the first part, and a plurality of second modems being arranged on the second part, which are connected in a data-technical manner to second coupling elements arranged on the second part, the first coupling elements extending over a respective first angular range when viewed in the circumferential direction around the axis of rotation, the first angular ranges, viewed from the first coupling element to the first coupling element, being disjoint in relation to one another and, viewed over the entirety of the first coupling elements, forming a full circle around the axis of rotation, the second coupling elements extending over a respective second angular range as viewed around the axis of rotation, the second angular ranges, as viewed around the axis of rotation, being disjoint in relation to one another and spaced apart from one another, in particular evenly distributed around the axis of rotation, so that the second coupling elements each couple with the first coupling element in whose first angular range the second angular range of the respective second coupling element is currently located.

According to one or more example embodiments, an operating method of the aforementioned type is designed in such a way that a switching state of a switching matrix arranged between the second coupling elements and the second modems is dynamically set by a setting facility in such a way that the first data is always transmitted between the same first and second modems.

The first part of the computed tomography system can be a fixed base body of the computed tomography system. In this case, the second part is the rotating gantry of the computed tomography system. Alternatively, the first part may be the rotating gantry of the computed tomography system. In this case, the second part is the fixed base body. Due to the fact that both assignments are possible, data can also be transmitted from the gantry to the base body or vice versa as required. Although data transmission from the gantry to the base body is the rule, transmissions in the reverse direction are also required.

In the context of one or more example embodiments, the number of second modems corresponds to the number of first modems. The first and second modems as such can be designed as so-called backbone modems, as they are known for communications systems, for example for communication between mobile radio masts. Such modems are optimized for varying signal paths and have internal digital signal processing, which consists of FIR filters, equalizers and FEC (forward error correction). An example of such a modem is a chip which is marketed by MaxLinear under the type designation BCM85110.

The number of first coupling elements likewise corresponds to the number of first modems as a rule. The number of second coupling elements, on the other hand, is greater than the number of first modems as a rule. In the best case, it is exactly 1 greater.

The first angular ranges are the same size as one another as a rule. If n refers to the number of first coupling elements, the first angular ranges thus each extend over 360°/n.

The extension of the second angular ranges, on the other hand, can be considerably smaller. However, if m refers to the number of second coupling elements, the second angular ranges preferably extend over a maximum of 360°/nm. Due to the preferably even distribution, the second coupling elements are preferably spaced apart from one another by 360°/m. If—for example, n—has the value 3 and m has the value 4, the second angular ranges should therefore preferably extend over a maximum of 360°/12=30° and be spaced apart from one another by 360°/4=90°.

The switching matrix must assign the m second coupling elements to the n second modems. A suitable switching matrix can be formed by a parallel arrangement of n switches, each of which can switch m inputs through to one (1) output. The respective output can be permanently connected to one of the n second modems. Corresponding switches are known. Reference can be made to the switch sold by MACOM under the type designation MASW-011152 purely by way of example.

Due to the repeated switching of the switching matrix, the jumps in the transmission behavior from the first to the second modem can be significantly reduced. As a result, the first data can be reconstructed in a high-quality manner. As a result, the quality of the data transmission can also be maintained during the rotation of the first part relative to the second part.

Preferably, the setting facility determines the switching state of the switching matrix as a function of a current angle of rotation of the first part relative to the second part. The current angle of rotation as such is therefore known to the setting facility and is used by the setting facility to determine the switching state of the switching matrix. This procedure is particularly simple.

In the simplest case, the dynamic setting of the switching matrix is carried out by the setting facility using only the angle of rotation of the first part relative to the second part. If necessary, however, the setting facility can also take into account at least one time derivative of the angle of rotation (i.e. the speed of rotation, the rotational acceleration, etc.) in addition to the angle of rotation as part of the determination of the switching state of the switching matrix.

It is possible for the angle of rotation to be measured in each case, i.e. for the determination of the setting of the switching matrix to be based on a measured angle of rotation in each case. In this case too, it is possible to also take into account at least one time derivative of the angle of rotation as part of the determination of the setting of the switching matrix.

Alternatively, it is possible for the angle of rotation to be measured only at predetermined angle positions, for example only every 120°, every 180°, or even only once per complete revolution of the first part relative to the second part. In this case, the angle of rotation between the predetermined angle positions is determined by the setting facility by updating the last measured angle of rotation on the basis of operating data characterizing the rotation, in particular the speed of rotation and/or the rotational acceleration.

Preferably, the data to be transmitted is supplied to the first or second modems as complex signals, and the first or second modems perform quadrature amplitude modulation of a carrier signal in accordance with the complex signals supplied to them. As a result, the data rate at which the first data can be transmitted can be maximized. In particular in conjunction with quadrature amplitude modulation, one or more example embodiments demonstrates its full advantages.

Preferably, distortion facilities arranged between the first modems and the first coupling elements and/or between the second modems and the second coupling elements are used to distort the respectively transmitted signal in accordance with a respective distortion rule. In this case, the respective distortion rule is set by the setting facility as a function of the angle of rotation of the first part relative to the second part.

The dynamic setting of the distortion rules by the setting facility can likewise be carried out as a direct function of the angle of rotation of the first part relative to the second part. If necessary, at least one time derivative of the angle of rotation can also be utilized in addition to the angle of rotation.

Such distortions can be used to compensate for the distortion of a data transmission caused by the transmission function of the respective transmission channel. As a result, an almost undistorted signal can be recovered so that a high-quality reconstruction of the first data is possible. Matched filtering therefore takes place. Such an approach is known in the prior art for quadrature amplitude modulation. In the present case, however, the distortion rules are tracked more or less continuously as a function of the angle of rotation of the first part relative to the second part. This allows the high quality of data transmission to be maintained even while the gantry is rotating.

The parameters required to set the distortion facilities can, for example, be stored in the setting facility in a lookup table for a multiplicity of input variables. As a rule, the input variables include at least the angle of rotation of the first part relative to the second part, and possibly also time derivatives of the angle of rotation.

Preferably, during the rotation of the first part relative to the second part, second data is also transmitted via the first and second coupling elements between third modems arranged on the first part and fourth modems arranged on the second part. In this case, the switching matrix is dynamically switched by the setting facility in such a way that the second data is always transmitted between the same third and fourth modems. This allows the transmission rate to be increased even further.

Preferably, the first and the second data is modulated onto carrier signals of various frequencies via the first to fourth modems before being supplied to the first and second coupling elements, so that the respectively occupied frequency ranges are disjoint in relation to one another.

The object is furthermore achieved by a computed tomography system with the features of claim 8. Advantageous embodiments of the computed tomography system are the subject of the dependent claims 7 to 14.

According to one or more example embodiments, a computed tomography system of the aforementioned type is designed in such a way that

- a switching matrix is arranged between the second coupling elements and the second modems and—the switching matrix is assigned a setting facility from which a switching state of the switching matrix is dynamically set in such a way that, during a data transmission of first data between the first and the second modems which takes place during the rotation of the first part relative to the second part around the axis of rotation, the first data is always transmitted between the same first and second modems.

The resulting facts and advantages correspond to those of the operating method according to one or more example embodiments.

The advantageous embodiments of the computed tomography system correspond to the advantageous embodiments of the operating method. The same applies to the resulting advantages.

According to FIG. 1, a computed tomography system 1 has a fixed base body 2. A gantry 3 is rotatably mounted on the base body 2 so that the gantry 3 can be rotated relative to the base body 2 around an axis of rotation 4. The rotatability is indicated by an arrow 5 in FIG. 1. The gantry 3 carries, as is generally customary, an X-ray source 6 and an X-ray detector 7. The X-ray source 6 and the X-ray detector 7 are diametrically opposite one other with respect to the axis of rotation 4. In some cases, the gantry 3 also carries a further X-ray source 8 and a further X-ray detector 9. The further X-ray source 8 and the further X-ray detector 9 are also diametrically opposite one other with regard to the axis of rotation 4. The other X-ray source 8 and the other X-ray detector 9, if they are present, are generally arranged offset by 90° in the circumferential direction around the axis of rotation 4 as viewed with respect to the first-mentioned X-ray source 6 and the first-mentioned X-ray detector 7. During the rotation of the gantry 3 around the axis of rotation 4, the X-ray detector 7 or the X-ray detectors 7, 9 can be used to capture X-ray images of an object of investigation 10 which is arranged in the area of the axis of rotation 4.

The base body 2 can be regarded as the first part in the sense of one or more example embodiments. In this case, the gantry 3 is a second part in the sense of one or more example embodiments. However, the reverse assignment is also possible. In connection with the embodiment explained above, data transmission from the gantry 3 to the base body 2 is explained below. In principle, however, data transmission from the base body 2 to the gantry 3 is also possible. The only decisive factor is always the relative mobility of the two parts 2, 3 in relation to one other and the transmission of data from one of the two parts 2, 3 to the other of the two parts 2, 3.

Figure 2:
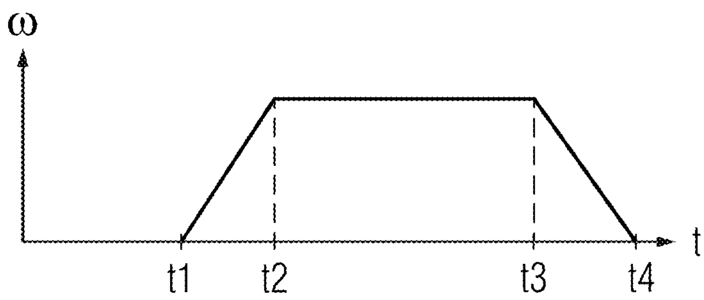
FIG. 2 shows a time diagram according to one or more example embodiments.

FIG. 2 shows the rotation of the gantry 3 as a function of time t. According to FIG. 2, rotation of the gantry 3 is started at a time t1 to capture the X-ray images of the object of investigation. Specifically, the gantry 3 is accelerated from the time t1 to the time t2 so that a speed of rotation ω reaches a maximum value at the time t2. The gantry 3 then rotates at the maximum speed of rotation up to a time t3 and is finally slowed down again until it comes to a standstill at a time t4.

Figure 3:
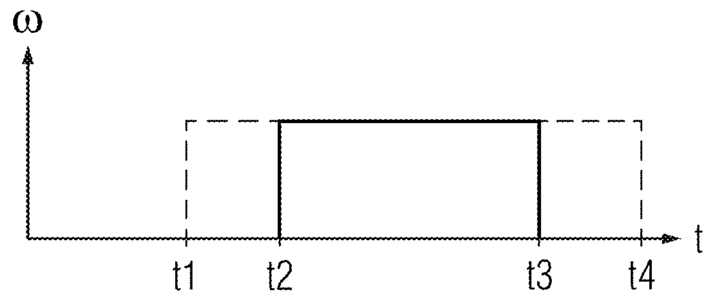
FIG. 3 shows a further time diagram according to one or more example embodiments.

The X-ray images are captured at least between the times t2 and t3, often even from the time t1 and up to the time t4. More or less simultaneously with the capturing of the X-ray images, the X-ray images are also transmitted according to FIG. 3 from the gantry 3 to the base body 2. FIG. 3 shows in a solid line the period of time during which at least the data transmission takes place, and in dashed lines the periods of time during which data transmission can likewise take place. The transmitted data is of a digital nature.

Figure 4:
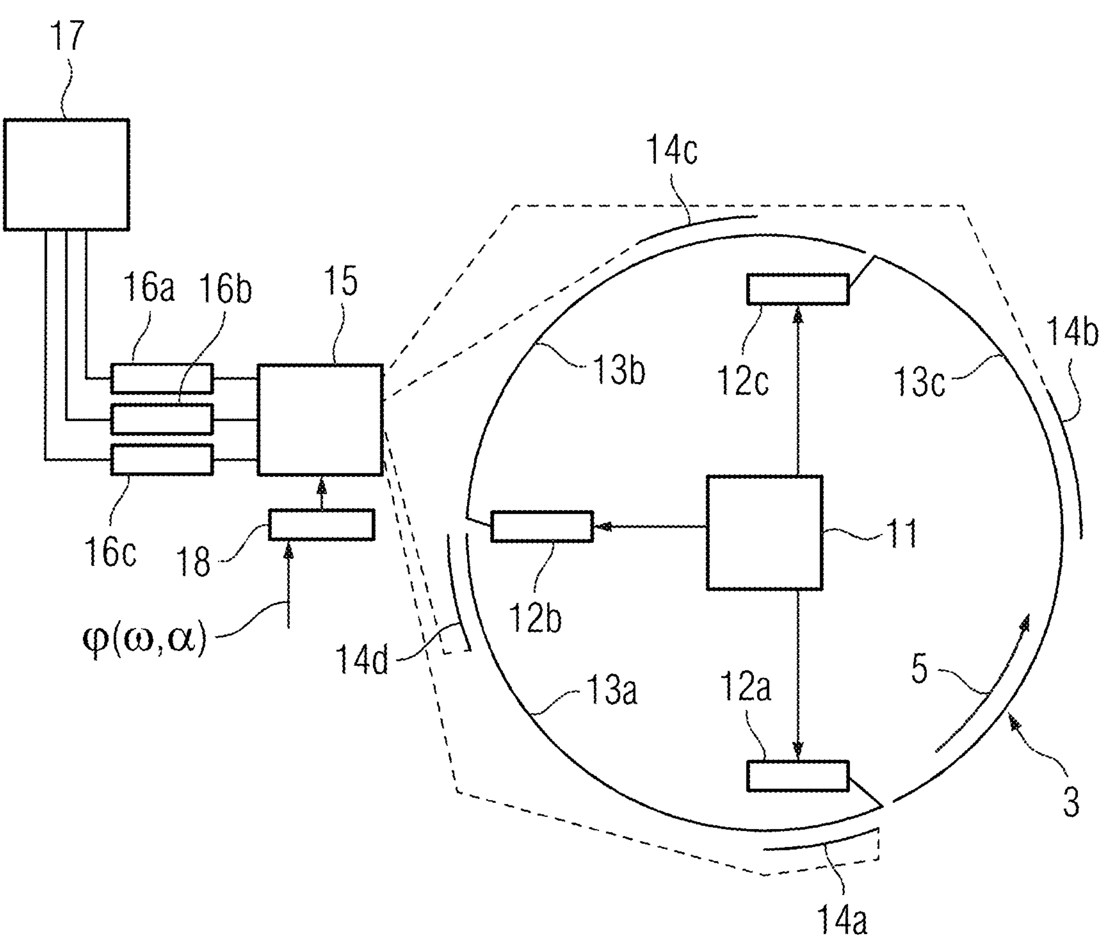
FIG. 4 shows a data transmission structure according to one or more example embodiments.

FIG. 4 shows in simplified form a structure for transmitting data between the gantry 3 and the base body 2.

According to FIG. 4, a data source 11 is present. The data source 11 can, for example, be a unit which receives the images from the X-ray detectors 7, 9 and processes them (slightly). The data source 11 is connected to a plurality of first modems 12 in a data-technical manner. In the present case, there are three first modems 12. The first modems 12 are connected in a data-technical manner to a respective first coupling element 13. The first coupling elements 13 each extend over 360°/n around the axis of rotation 4, n being the number of first modems 12 or first coupling elements 13. The angular range over which a respective first coupling element 13 extends is disjoint to the angular ranges over which the other first coupling elements 13 extend. Together, the aforementioned angular ranges form a full circle. The first coupling elements 13 may, for example, be designed as dielectric conductors or as slotted waveguides. The data source 11, the first modems 12 and the first coupling elements 13 are arranged on the gantry 3.

The first coupling elements 13 couple with second coupling elements 14. The number of second coupling elements 14 is usually greater than the number of first coupling elements 13. In the present case, the number of second coupling elements 14 is 4, i.e. greater by 1 than the number of first coupling elements 13. The second coupling elements 14 also extend over a respective angular range when viewed around the axis of rotation 4. However, these angular ranges are considerably smaller than the angular ranges over which the first coupling elements 13 extend. Ideally, the angular ranges are very small (only a few degrees). The angular ranges over which the second coupling elements 14 extend are in any case disjoint and spaced apart from one another. Preferably, the angular ranges are evenly distributed around the axis of rotation 4.

The second coupling elements 14 are connected to second modems 16 in a data-technical manner via a switching matrix 15. The switching matrix 15 is therefore arranged between the second coupling elements 14 and the second modems 16. The second modems 16 are in turn connected to a data sink 17 in a data-technical manner. The second coupling elements 14 and the second modems 16 are—like the switching matrix 15—arranged on the base body 2.

The first modems 12, the first coupling elements 13 and the second modems 16 are each provided with a suffix a to c in FIG. 4 in order to be able to distinguish them from one another. For the same reasons, the second coupling elements 14 are each provided with a suffix a to d in FIG. 4.

It can be seen from the above explanations that the data is transmitted between the first modems 12 and the second modems 16 via the first coupling elements 13 and the second coupling elements 14. Furthermore, it can be seen that a coupling between one of the first coupling elements 13 and one of the second coupling elements 14 only exists if the angular range covered by the respective second coupling element 14 is located in the angular range covered by the respective first coupling element 13. The coupling of the first and second coupling elements 13, 14 with one other therefore varies during the rotation of the gantry 3. This is explained in more detail below in conjunction with FIGS. 5 to 7. For the purposes of this explanation, it is assumed that the configuration shown in FIG. 4 is given, i.e. that a total of three first coupling elements 13 are present, the first coupling elements 13 each extend over 120°, a total of four second coupling elements 14 are present, the second coupling elements 14 are each offset by 90° relative to one another and the second coupling elements 14 each extend over 30°.

Figure 5:
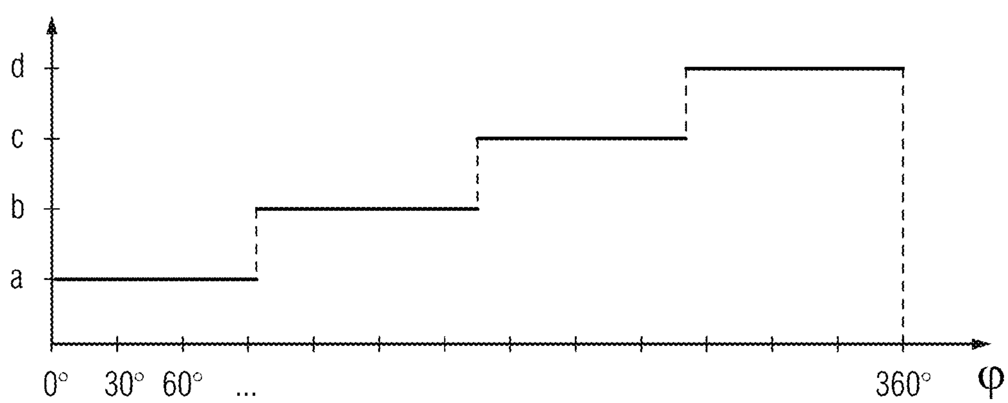
FIG. 5 shows an angle diagram according to one or more example embodiments.
Figure 6:
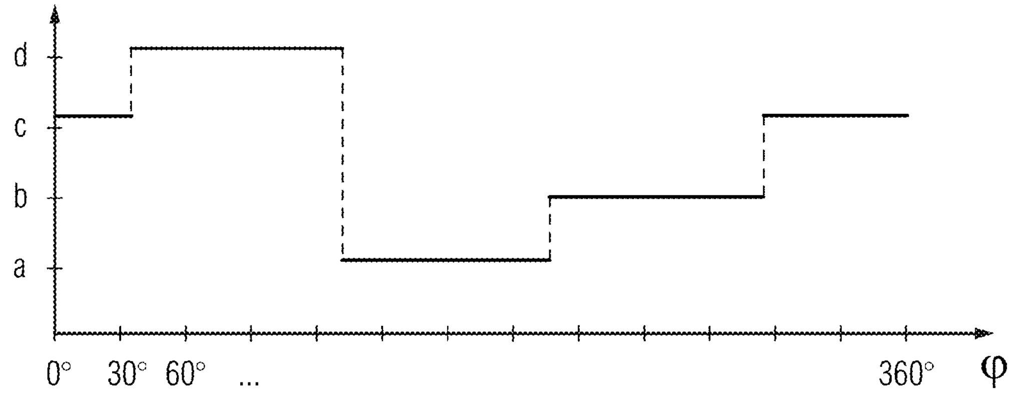
FIG. 6 shows an angle diagram according to one or more example embodiments.

In FIGS. 5 to 7, the angle of rotation $\varphi$ from 0° to 360° is plotted on the abscissa in each case. An angle of rotation $\varphi$ of 0° may correspond, for example, to the rotational position shown in FIG. 4. A counterclockwise rotation should correspond to an increase in the angle of rotation $\omega$. The ordinate shows to which of the second coupling elements 14 the respective first coupling element 13 is coupled. FIGS. 5 to 7 show—in this order—the coupling for the first coupling element 13*a*, the first coupling element 13*b* and the first coupling element 13*c*.

A switching state of the switching matrix 15 is based on the situation described above in connection with FIGS. 5 to 7: The switching state is dynamically set by a setting facility 18 (see FIG. 4) assigned to the switching matrix 15 in such a way that the data is always transmitted between the same first and second modems 12, 16. The second modem 16*a* is therefore always connected to the second coupling element 14 which is currently receiving data from the first modem 12*a* via the first coupling element 13*a*. Similarly, the second modem 16*b* is always connected to the second coupling element 14 which is currently receiving data from the first modem 12*b* via the first coupling element 13*b*. And the second modem 16*c* is also always connected to the second coupling element 14 which is currently receiving data from the first modem 12*c* via the first coupling element 13*c*. The same would also apply for communication in the reverse direction.

In order to be able to determine the switching state of the switching matrix 15 and therefore to be able to set the switching matrix 15 accordingly, the angle of rotation $\varphi$ of the gantry 3 must be known directly or indirectly to the setting facility 18. In the simplest case, the angle of rotation $\varphi$ is supplied directly to the setting facility 18. If necessary, the speed of rotation $\omega$ and/or the rotational acceleration $\alpha$ can also be supplied to the setting facility 18—either additionally or alternatively. In this case, the setting facility 18 can take these values $\omega$, $\alpha$ into account during determination or (for example, in conjunction with a reference pulse which is emitted once per revolution when a reference rotational position is passed) determine the angle of rotation $\varphi$. By additionally taking into account the speed of rotation $\omega$ and/or the rotational acceleration $\alpha$, any time offsets can be better taken into account.

As shown in FIG. 8, the data source 11 supplies a data stream DS (i.e. the data to be transmitted, see FIG. 10) to the respective first modem 12, preferably as a complex signal. The data stream DS thus comprises two partial signals DS1, DS2, which represent the real part and the imaginary part of the complex signal. In this case, the respective first modem 12 is designed as a quadrature amplitude modulator. It comprises two multipliers 19, to which the cosine and the sine of a carrier signal CS are supplied. Furthermore, one of the two partial signals DS1, DS2 is supplied to each of the two multipliers 19. The signals generated by the two multipliers 19 are supplied to an adder 20, which adds the two signals to form a transmission signal SS. The transmission signal SS is transmitted via the respective first coupling element 13 and the respective second coupling element 14 to the corresponding second modem 16.

In the case of quadrature amplitude modulation, the second modems 16 and the data sink 17 are also designed accordingly, as shown in FIG. 9. In particular in this case, the respective second modem 16 comprises two multipliers 21, to which the transmitted signal DS' (see FIG. 10) and the cosine and the sine of a further carrier signal CS' having the same frequency as the carrier signal CS are supplied. The two multipliers 21 provide the real part DS1' and the imaginary part DS2' of the demodulated signal as output signals, on which a respective high-frequency component is superimposed. The respective high-frequency component is filtered out in a respective low-pass filter 22, so that the real part DS1' and the imaginary part DS2' of the demodulated (complex) signal are available at the output of the respective low-pass filter 22. The two partial signals DS1', DS2' are supplied to the data sink 17.

Figure 10:
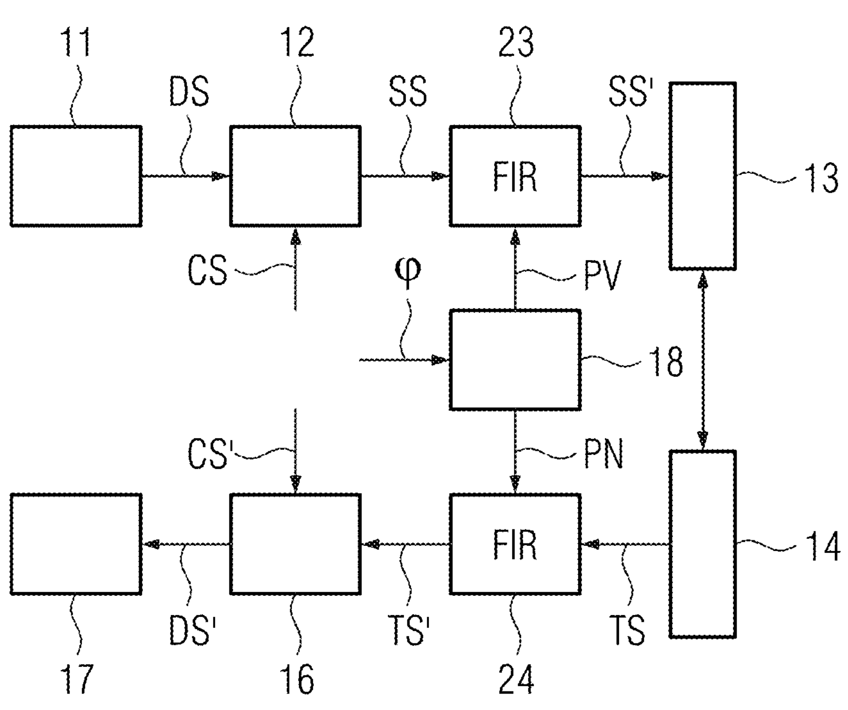
FIG. 10 shows a communication channel according to one or more example embodiments.

According to FIG. 10, the data is transmitted in the form of a data stream DS from the data source 11 via one of the first modems 12, the associated first coupling element 13 and one of the second coupling elements 14 to the corresponding second modem 16, to the data sink 17. The switching matrix 15 is not shown in FIG. 10. However, it is present.

For correct demodulation, the phase of the further carrier signal CS' must match the phase of the carrier signal CS. For this purpose, first distortion facilities 23 can be arranged between the first modems 12 and the first coupling elements 13 as shown in FIG. 10. Alternatively or additionally, second distortion facilities 24 may be arranged between the second coupling elements 14 and the second modems 16. The distortion facilities 23, 24 can in particular be embodied as FIR filters. The exact sequence of data transmission is thus as follows:

The data source 11 transmits the data stream DS to the corresponding first modem 12. The data stream DS can, see the embodiments relating to FIG. 8, be embodied in particular as a complex signal. The first modem 12 modulates the carrier signal CS according to the data stream DS. The modulated carrier signal corresponds to the transmission signal SS which the first modem 12 is to feed into the first coupling element 13 from the base. However, the transmission signal SS is first supplied to the first distortion facility 23, which distorts the transmission signal SS according to a first distortion rule. Only the distorted transmission signal—hereinafter provided with the reference character SS' to distinguish it from the original transmission signal SS—is supplied to the corresponding first coupling element 13.

In an analogous manner, the transmitted signal TS is first supplied to the second distortion facility 24. The second distortion facility 24 distorts the transmitted signal TS according to a second distortion rule. Only the distorted transmitted signal-hereinafter provided with the reference character TS' to distinguish it from the original transmitted signal TS—is supplied to the corresponding second modem 16. The second modem 16 demodulates the distorted transmitted signal TS' and thereby generates a transmitted data stream DS'. The transmitted data stream DS' is supplied to the data sink 16.

The distortion facilities 23, 24 can be parameterized with parameters PV, PN. The parameters PV determine the first distortion rule. Similarly, the parameters PN determine the second distortion rule.

As already mentioned, the data transmissions take place while the gantry 3 is rotating. As a result, the area of the respective first coupling element 13, at which the respective adjacent second coupling element 14 couples with the respective first coupling element 13, changes continuously during the data transmissions. As a result, the effective length of the transmission channel from the respective first modem 12 to the respective second modem 16 changes continuously during the rotation of the gantry 3. Consequently, the transmission properties of the transmission channel also change. The purpose of the procedure of FIG. 10 is to keep the transmission properties of the entirety of the first distortion facility 23, transmission channel and second distortion facility 24 constant or at least substantially constant by correspondingly setting the distortion facilities 23, 24 or correspondingly specifying the parameters PV, PN.

To keep the parameters constant, it is also necessary to set the parameters PV, PN dynamically while the gantry 3 is rotating. As can be seen from FIG. 10, the setting can be carried out in particular by the setting facility 18. The setting can be carried out in particular as a function of the angle of rotation $\varphi$, if necessary with additional consideration of the speed of rotation $\omega$ and/or the rotational acceleration $\alpha$. The corresponding embodiments for setting the switching matrix 15 can be applied in an analogous manner.

Determining the respective setting of the switching matrix 15 is relatively simple. Determining the parameters PV, PN, on the other hand, can be considerably more complex and must also be carried out much more frequently. Preferably, therefore, a lookup table is stored in the setting facility 18, in which the parameters PV, PN are stored for certain values of the angle of rotation $\varphi$, and possibly also for certain values of the speed of rotation $\omega$ and/or the rotational acceleration $\alpha$. The use of a lookup table ensures real-time capability in a simple way.

The basic principle for determining the parameters PV, PN is explained below.

If H, U and V refer to the transmission functions of the transmission channel, the first distortion facility 23 and the second distortion facility 24, then H'=UHV always applies, H' being the resulting transmission function of the first distortion facility 23, the transmission channel and the second distortion facility 24. Ideally, the relationship H'=I should continue to apply, where I is the unit transmission function.

The transmission function H of the transmission channel is variable in time due to the rotation of the gantry 3. The parameters PV, PN, with which the two distortion facilities 23, 24 are parameterized and which therefore determine the corresponding distortion rules and thus their transmission functions U, V, should therefore be determined at all times in such a way that the aforementioned relationship H'=I applies exactly or at least approximately.

Depending on the situation, it may be sufficient if only either the first distortion facility 23 is present or the second distortion facility 24 is present or both distortion facilities 23, 24 are present, but only the parameters PV, PN of one of the two distortion facilities 23, 24 are repeatedly reset. As a rule, however, it is preferable if both distortion facilities 23, 24 are present and the parameters PV, PN, of both distortion facilities 23, 24 are also repeatedly reset.

Figure 11:
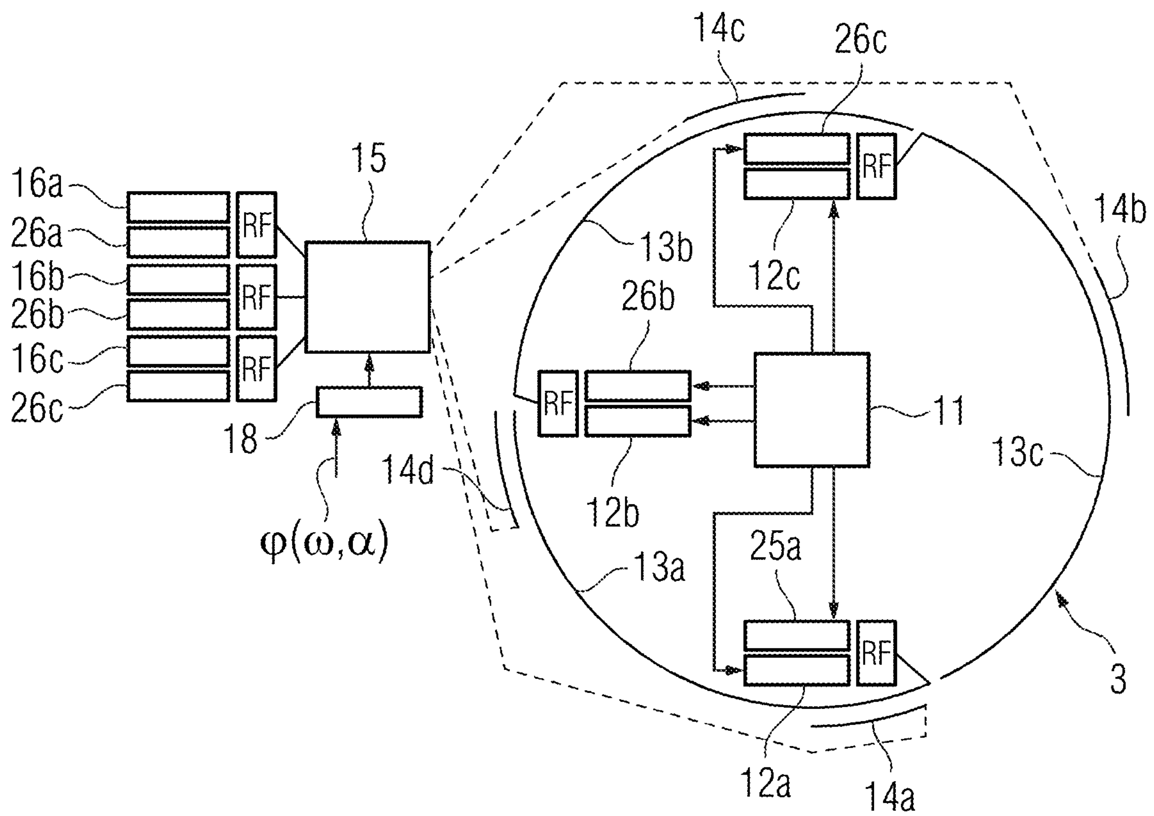
FIG. 11 shows a further data transmission structure according to one or more example embodiments.

FIG. 11 shows a modification of the data transmission structure of FIG. 4. According to FIG. 11, a plurality of third modems 25 is arranged on the gantry 3. As a rule, the number of third modems 25 corresponds to the number of first modems 12. The third modems 25 are connected to the first coupling elements 13 in a data-technical manner. Analogously, a plurality of fourth modems 26 is arranged on the base body 2. The number of fourth modems 26 corresponds to the number of third modems 25. The fourth modems 26 are connected to the second coupling elements 14 via the switching matrix 15 in a data-technical manner. Analogous to the procedure for the first and second modems 12, 16, the switching matrix 15 is dynamically switched by the setting facility 18 during the rotation of the gantry 3 in such a way that further data is always transmitted between the same third and fourth modems 25, 26. Data is therefore always transmitted between the third modem 25*a* and the fourth modem 26*a*, between the third modem 25*b* and the fourth modem 26*b* and between the third modem 25*c* and the fourth modem 26*c*. Thus, during the rotation of the gantry 3, further additional communication can be realized via the first and second coupling elements 13, 14 in a completely analogous manner. Communication can take place in the same direction as data transmission between the first and second modems 12, 16, i.e. from the third modems 25 to the fourth modems 26. However, it is also possible to realize data transmission in the other direction, so that simultaneous data transmissions therefore take place in opposite directions.

Figure 12:
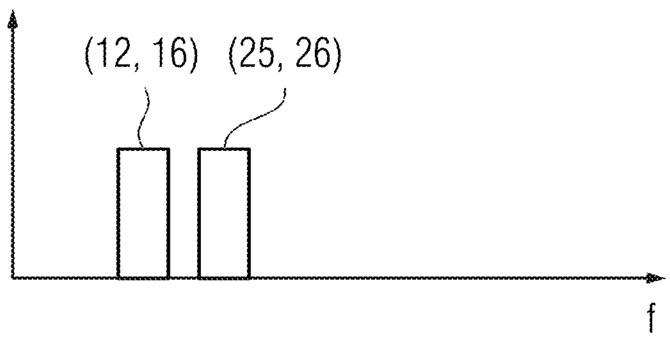
FIG. 12 shows a frequency diagram according to one or more example embodiments and FIG. 13 shows a further frequency diagram according to one or more example embodiments.

In order to realize the two data transmissions via a respective first coupling element 13, the corresponding data is modulated onto carrier signals of different frequencies via the corresponding modems 12, 25 or 12, 26 before being supplied to the first and second coupling elements 13, 14, so that the respectively occupied frequency ranges are disjoint in relation to one another. FIG. 12 shows this as an example of a pairing of one of the first modems 12 and one of the second modems 16, on the one hand, and a pairing of one of the third modems 25 and one of the fourth modems 26, on the other hand. It can be seen that the frequencies f which are used for data transmission between the corresponding first modem 12 and the corresponding second modem 16 are disjoint from the frequencies f which are used for data transmission between the corresponding third modem 25 and the corresponding fourth modem 26.

Figure 13:
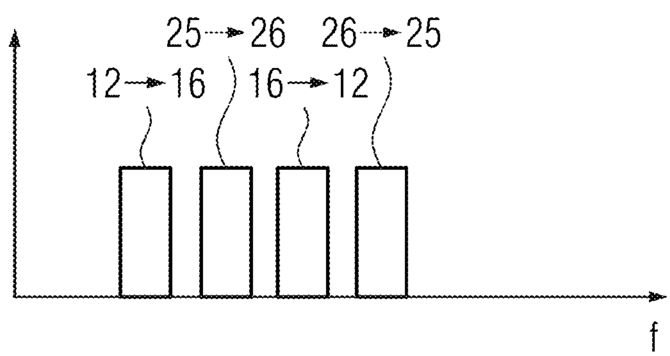

It is even possible, as shown in FIG. 13, to transmit data simultaneously in both directions via both pairings of modems 12, 16, 25, 26, provided that the basic condition that the respectively occupied frequency ranges are disjoint in relation to one another is maintained.

In summary, one or more example embodiments thus relates to the following subject matter.

During a rotation of a first part 3 of a computed tomography system 1 relative to a second part 2 of the computed tomography system 1 around an axis of rotation 4, data is transmitted between first modems 12 arranged on the first part 3 and second modems 16 arranged on the second part 2 via first coupling elements 13 arranged on the first part 3 and second coupling elements 14 arranged on the second part 2. The first coupling elements 13 extend over a respective first angular range when viewed in the circumferential direction around the axis of rotation 4. Viewed from the first coupling element 13 to the first coupling element 13, these angular ranges are disjoint in relation to one another and, viewed over the entirety of the first coupling elements 13, form a full circle around the axis of rotation 4. The second coupling elements 14 extend over a respective second angular range as viewed around the axis of rotation 4. The second angular ranges, as viewed around the axis of rotation 4, are disjoint in relation to one another and spaced apart from one another. Thus, the second coupling elements 14 each couple with the first coupling element 13 in whose first angular range the second angular range of the respective second coupling element 14 is currently located. A switching state of a switching matrix 15 arranged between the second coupling elements 14 and the second modems 16 is dynamically set by a setting facility 18 in such a way that the first data is always transmitted between the same first and second modems 12, 16.

One or more example embodiments has many advantages. In particular, comparatively simple and yet robust data transmission is created, via which high transmission rates in the range of several gigabits per second can be realized. The measures according to one or more example embodiments are also suitable without further ado for retrofitting to an existing computed tomography system which is not yet according to one or more example embodiments.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative used descriptors herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, JavaR, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although the invention has been illustrated and described in more detail by at least some example embodiments, the invention is not limited by the disclosed examples and other variations may be derived therefrom by a person skilled in the art without departing from the scope of the invention.

The invention claimed is:

1. An operating method for a computed tomography system, the method comprising:

transmitting first data via a plurality of first coupling elements on a first part of the computed tomography system and a plurality of second coupling elements on a second part of the computed tomography system during a rotation of the first part of the computed tomography system relative to the second part of the computed tomography system around an axis of rotation between a plurality of first modems on the first part and a plurality of second modems on the second part, wherein the first coupling elements extend over a respective first angular range when viewed in a circumferential direction around the axis of rotation, the first angular ranges, viewed from the first coupling element to the first coupling element, are separated in relation to one another and, viewed over the entirety of the first coupling elements, form a full circle around the axis of rotation, the second coupling elements extend over a respective second angular range as viewed around the axis of rotation, the second angular ranges, as viewed around the axis of rotation, are separated in relation to one another and spaced apart from one another such that the second coupling elements each couple with the first coupling element in whose first angular range the second angular range of the respective second coupling element is currently located; and dynamically setting a switching state of a switching matrix between the second coupling elements and the second modems by a setting facility such that the first data is always transmitted between the same first and second modems.

2. The operating method of claim 1, wherein the setting includes determining the switching state of the switching matrix as a function of an angle of rotation of the first part relative to the second part.

3. The operating method of claim 2, wherein the determining the switching state is based on at least one time derivative of the angle of rotation in addition to the respective angle of rotation when determining the switching state of the switching matrix.

4. The operating method of claim 1, wherein the data to be transmitted is supplied to the first or second modems as complex signals, and the first or second modems perform quadrature amplitude modulation of a carrier signal in accordance with the complex signals.

5. The operating method of claim 1, wherein via distortion facilities at least one of between the first modems and the first coupling elements or between the second modems and the second coupling elements, a respectively transmitted signal is distorted in accordance with a respective distortion rule, and the respective distortion rule is set by the setting facility as a function of the angle of rotation of the first part relative to the second part.

6. The operating method of claim 1, wherein during the rotation of the first part relative to the second part, second data is transmitted via the first and second coupling elements between third modems on the first part and fourth modems on the second part, and the switching matrix is dynamically switched by the setting facility such that the second data is always transmitted between the same third and fourth modems.

7. The operating method of claim 6, wherein the first data and the second data are modulated onto carrier signals of different frequencies via the first, the second, the third and the fourth modems before being fed to the first and second coupling elements such that frequency ranges occupied in each case are separated in relation to one another.

8. A computed tomography system, comprising:
- a first part;
- a second part, wherein
  - the first part is rotatable relative to the second part around an axis of rotation;
- a plurality of first modems on the first part which are connected in a data-technical manner to first coupling elements on the first part;
- a plurality of second modems on the second part which are connected in a data-technical manner to second coupling elements on the second part, wherein
  - the first coupling elements extend over a respective first angular range when viewed in the circumferential direction around the axis of rotation,
  - the first angular ranges, viewed from the first coupling element to the first coupling element, are separated in relation to one another and, viewed over the entirety of the first coupling elements, form a full circle around the axis of rotation,
- the second coupling elements extend over a respective second angular range as viewed around the axis of rotation,
- the second angular ranges, as viewed around the axis of rotation, are separated in relation to one another and spaced apart from one another such that the second coupling elements each couple with the first coupling element in whose first angular range the second angular range of the respective second coupling element is currently located; and
- a switching matrix is between the second coupling elements and the second modems and the switching matrix is assigned a setting facility, by which a switching state of the switching matrix is dynamically set such that during data transmission of first data between the first and the second modems, which takes place during the rotation of the first part relative to the second part around the axis of rotation, the first data is always transmitted between the same first and second modems.

9. The computed tomography system of claim 8, wherein the setting facility is configured to determine the switching state of the switching matrix as a function of an angle of rotation of the first part relative to the second part.

10. The computed tomography system of claim 9, wherein the setting facility is configured to determine the switching state of the switching matrix based on at least one time derivative of the angle of rotation in addition to the respective angle of rotation.

11. The computed tomography system of claim 8, wherein the data to be transmitted is supplied to the first or second modems as complex signals, and in that the first or second modems are designed as quadrature amplitude modulators configured to perform quadrature amplitude modulation of a carrier signal in accordance with the complex signals.

12. The computed tomography system of claim 8, wherein distortion facilities are at least one of between the first modems and the first coupling elements or between the second modems and the second coupling elements via which a distortion of the respectively transmitted signal takes place in accordance with a respective distortion rule, and the respective distortion rule is set by the setting facility as a function of the angle of rotation of the first part relative to the second part.

13. The computed tomography system of claim 8, wherein a plurality of third modems is on the first part, which is connected to the first coupling elements in a data-technical manner, and a plurality of fourth modems is on the second part, which is connected to the second coupling elements in a data-technical manner via the switching matrix, such that during the rotation of the first part relative to the second part, second data is additionally transmitted between the third modems and the fourth modems via the first and second coupling elements, and in that the switching matrix is dynamically switched by the setting facility such that, during data transmission of the second data which takes place during the rotation of the first part relative to the second part, the second data is always transmitted between the same third and fourth modems.

14. The computed tomography system of claim 13, wherein the first data and the second data are modulated onto carrier signals of different frequencies via the first, the second, the third and the fourth modems before being fed to the first and second coupling elements, such that frequency ranges occupied in each case are separated in relation to one another.

15. The method of claim 1, wherein the second angular ranges are evenly distributed around the axis of rotation.

16. The computed tomography system of claim 8, wherein the second angular ranges are evenly distributed around the axis of rotation.

* * * * *